United States Patent
Jerebko et al.

(10) Patent No.: US 7,840,046 B2
(45) Date of Patent: Nov. 23, 2010

(54) SYSTEM AND METHOD FOR DETECTION OF BREAST MASSES AND CALCIFICATIONS USING THE TOMOSYNTHESIS PROJECTION AND RECONSTRUCTED IMAGES

(75) Inventors: Anna Jerebko, West Chester, PA (US); Arun Krishnan, Exton, PA (US); Xiang Zhou, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 820 days.

(21) Appl. No.: 11/767,707

(22) Filed: Jun. 25, 2007

(65) Prior Publication Data

US 2008/0025592 A1    Jan. 31, 2008

Related U.S. Application Data

(60) Provisional application No. 60/816,710, filed on Jun. 27, 2006.

(51) Int. Cl.
 G06K 9/00 (2006.01)
 A61B 6/04 (2006.01)
 A61B 5/05 (2006.01)

(52) U.S. Cl. ........................... 382/128; 378/37; 600/410

(58) Field of Classification Search ................. 382/128, 382/129, 130, 131, 132, 133, 134; 378/37, 378/46, 90, 92, 98.4, 98.6, 98.9, 101, 140; 600/407, 410, 425; 604/74, 346; 128/915, 128/920, 922
See application file for complete search history.

(56) References Cited

U.S. PATENT DOCUMENTS

| | | | | |
|---|---|---|---|---|
| 5,003,979 | A * | 4/1991 | Merickel et al. | 600/410 |
| 5,537,485 | A * | 7/1996 | Nishikawa et al. | 382/130 |
| 7,467,119 | B2 * | 12/2008 | Saidi et al. | 706/21 |
| 2003/1194121 | | 10/2003 | Eberhard | |

OTHER PUBLICATIONS

Peters et al., "Reconstruction-Independent 3D CAD for Calcification Detection in Digital Breast Tomosynthesis Using Fuzzy Particles", Progress in Pattern Recognition, Image Analysis and Applications, Lecture Notes in Computer Science, Springer-Verlag, BE, vol. 3773, Oct. 24, 2005, pp. 400-408.

(Continued)

*Primary Examiner*—Abolfazl Tabatabai

(57) ABSTRACT

A method of detecting breast masses and calcifications in digitized images, includes providing a plurality of 2-dimensional (2D) digital X-ray projectional breast images acquired from different viewing angles, extracting candidate lesions and 2D features from said 2D projectional images, computing spicularity characteristics of said candidate lesions, including location, periodicity, and amplitude, applying learning algorithms to said candidate lesions to predict a probability of malignancy of said lesion, receiving from said learning algorithm a probability map of detections for each breast image, said detections comprising associating pixels with a probability of being associated with a malignancy, creating a synthetic 2D slice for each X-ray image wherein malignant regions are indicated by ellipses on a non-malignant background, and constructing a synthetic 3-dimensional (3D) image volume from said 2D synthetic slices.

22 Claims, 3 Drawing Sheets

OTHER PUBLICATIONS

Leichter et al., "Improved Mammographic Interpretation of Masses Using Computer-Aided Diagnosis", European Radiology 2000, vol. 10, No. 2, Jan. 1, 2000, pp. 377-383.

Chan et al., "Computer-aided detection system for breast masses on digital tomosynthesis mammograms: preliminary experience", Radiology Dec. 2005, vol. 237, No. 3, pp. 1075-1080.

Jerebko et al., "Feasibility study of breast tomosynthesis CAD system", Progress in Biomedical Optics and Imaging, Proceedings of SPIE, Medical Imaging 2007, Computer-Aided Diagnosis 2007, vol. 6514, Feb. 20, 2007.

* cited by examiner

SYSTEM AND METHOD FOR DETECTION OF BREAST MASSES AND CALCIFICATIONS USING THE TOMOSYNTHESIS PROJECTION AND RECONSTRUCTED IMAGES

CROSS REFERENCE TO RELATED UNITED STATES APPLICATIONS

This application claims priority from "A method for detection of breast masses and calcifications using the Tomosynthesis projection and reconstructed images", U.S. Provisional Application No. 60/816,710 of Jerebko, et al., filed Jun. 27, 2006, the contents of which are herein incorporated by reference.

TECHNICAL FIELD

This disclosure is directed to computer aided detection of masses and calcifications in tomosynthesis images.

DISCUSSION OF THE RELATED ART

Mammography is the process of using low-dose X-rays (usually around 0.7 mSv) to examine the human breast. It is used to look for different types of tumors and cysts. Mammography has been proven to reduce mortality from breast cancer. Like all x-rays, mammograms use doses of ionizing radiation to create this image. Radiologists then analyze the image for any abnormal growths. It is normal to use longer wavelength X-rays than those used for radiography of bones. During the procedure, the breast is compressed by a dedicated mammography machine to even out the tissue, to increase image quality, and to hold the breast still to preventing motion blur. Both front and side images of the breast are taken. Deodorant, talcum powder or lotion may show up on the X-ray as calcium spots, and women are discouraged from applying these on the day of their investigation. The radiation exposure associated with mammography is a potential risk of screening. The risk of exposure appears to be greater in younger women. Until some years ago, mammography was typically performed with screen-film cassettes. Now, mammography is undergoing transition to digital detectors, known as Full Field Digital Mammography. Mammography has a false-negative rate of at least 10 percent. This is partly due to dense tissues obscuring the cancer and the fact that the appearance of cancer on mammograms has a large overlap with the appearance of normal tissues. However, mammography along with physical breast examination is still the modality of choice for screening for early breast cancer. It is the gold-standard which other imaging tests are compared with. Computed tomography, in which digital geometric processing is used to generate a three-dimensional image from a series of two-dimensional X-ray images taken around a single axis of rotation, has no real role in diagnosing breast cancer at the present.

While mammography is the only breast cancer screening method that has been shown to save lives, it is not perfect. Estimates of the numbers of cancers missed by mammography are usually around 10%-20%. This means that of the 350 per 100,000 women who have breast cancer, about 35-70 will not be seen by mammography. Reasons for not seeing the cancer include observer error, but more frequently it is due to the fact that the cancer is hidden by other dense tissue in the breast and even after retrospective review of the mammogram, cannot be seen. Furthermore, one form of breast cancer, lobular cancer, has a growth pattern that produces shadows on the mammogram which are indistinguishable from normal breast tissue.

Part of the difficulty in interpreting mammograms in younger women stems from the problem of breast density. Radiographically, a dense breast has a preponderance of glandular tissue, and younger age or estrogen hormone replacement therapy contribute to mammographic breast density. After menopause, the breast glandular tissue is gradually replaced by fatty tissue, making mammographic interpretation much more accurate. It has been speculated that part of the contribution of estrogen hormone replacement therapy to breast cancer mortality arises from the issue of increased mammographic breast density. Breast density is an independent adverse prognostic factor on breast cancer prognosis.

Breast tomosynthesis is one of the most exciting research developments in radiology in recent years. Breast tomosynthesis is a 3-dimensional (3D) imaging technique that can reduce the tissue overlap effect of conventional 2D mammogram, thus potentially reducing the false positive rate and the resulting required biopsies while still improving detection sensitivity. To start, X-ray images (original projection images) are acquired from multiple viewing angles. A motorized system takes a modified x-ray tube and moves it up vertically while pivoting the tube to keep it pointed toward the phantom and digital detector at image right. During an upward sweep, many separate digital chest images can be acquired in a relatively short time period (on order of 10 seconds). The system then resets its position slowly. The total exposure is the same as a single lateral chest radiograph. The 2D X-ray images are subsequently reconstructed into a 3D image consisting of 2D consecutive slices.

Due to the increased number of images, typically at least 10 times the number as compared to conventional mammography, the radiologist's workload increases dramatically. The computer aided detection of masses and calcifications could serve as a second viewer to increase the sensitivity of a radiologist.

Breast tomosynthesis allows a radiologist to detect and characterize suspicious lesions better, because it removes overlapping normal tissue which might otherwise obscure the lesions. The goal is to provide 3D information at the same high resolution and reasonable dose as mammography, while possibly reducing compression for improved patient comfort. Since the system will be based on digital mammography, it will also be faster and cheaper than alternatives requiring dedicated equipment such as CT or MR. For these reasons, breast tomosynthesis may be the first technique that can actually replace mammography in the near future, providing improved sensitivity and specificity of breast cancer diagnosis.

SUMMARY OF THE INVENTION

Exemplary embodiments of the invention as described herein generally include methods and systems for computer aided detection of masses and calcifications in tomosynthesis images.

According to an aspect of the invention, there is provided a method of detecting breast masses and calcifications in digitized images, including providing a plurality of 2-dimensional (2D) digital X-ray projectional breast images acquired from different viewing angles, each said X-ray projectional image comprising a set of intensities on a 2D grid of pixels, extracting candidate lesions and 2D features from said 2D projectional images, computing spicularity characteristics of said candidate lesions, said characteristics including, but not limited to, location, periodicity, and amplitude, applying machine learning algorithms to said candidate lesions to predict a probability of malignancy of said lesion, wherein said learning algorithms have been trained on a training set containing known examples of the features for lesions identified by a physician, receiving from said learning algorithm a probability map of detections for each breast image, said detections comprising associating pixels with a probability of being associated with a malignancy, creating a synthetic 2D slice for each X-ray image wherein malignant regions are indicated by ellipses on a non-malignant background, and constructing a synthetic 3-dimensional (3D) image volume from said 2D synthetic slices.

According to a further aspect of the invention, the probability map associates each pixel on each 2D X-ray image with a probability of being associated with a malignancy.

According to a further aspect of the invention, the probability map returns a list of pixel locations and associated malignancy probabilities, wherein only those locations with malignancy probabilities above a threshold are returned.

According to a further aspect of the invention, the method comprises constructing a 3D image from said 2D X-ray breast images, and superimposing said 3D synthetic image on said constructed 3D X-ray image.

According to a further aspect of the invention, the method comprises thresholding said detections in said 3D synthetic image wherein only those detections whose probability is above said threshold are visualized.

According to a further aspect of the invention, the malignancy probability in said malignant regions are represented by Gaussian functions inside said ellipses, wherein a peak amplitude of each said Gaussian corresponds to the pixel within said ellipse with a maximum probability of being associated with said malignancy, and whose probability amplitude decreases smoothly to a background value.

According to a further aspect of the invention, constructing said synthetic 3D image comprises seeking those 2D ellipses in those 2D synthetic slices that overlap in said 3D synthetic image, representing those 3D regions formed by overlapping 2D ellipses by 3D ellipsoids, representing the malignancy probability within each 3D ellipsoid by a 3D Gaussian whose probability amplitude decreases smoothly from a peak value within said ellipsoid to a background value.

According to a further aspect of the invention, the spicularity characteristics are computed using a spherical or polar coordinate transformation on said lesion followed by band pass filtering on the intensity or gradient of said transformed lesion.

According to a further aspect of the invention, the method comprises enhancing said X-ray breast images prior to extracting said 2D features.

According to another aspect of the invention, there is provided a method of detecting breast masses and calcifications in digitized images, including providing a plurality of 2-dimensional (2D) digital X-ray breast images acquired from different viewing angles, said X-ray image comprising a set of intensities on a 2D grid of pixels, constructing a 3-dimensional (3D) image volume from said 2D X-ray breast images, computing spicularity characteristics of said candidate lesions, said characteristics including, but not limited to, location, periodicity, and amplitude, extracting 3D features from said image volume using a machine learning algorithm, applying machine learning algorithms to said candidate lesions to predict a probability of malignancy of said lesion, wherein said learning algorithms have been trained on a training set containing known examples of the features for lesions identified by a physician, receiving from said learning algorithm a probability map of detections for each breast image, said detections comprising associating pixels with a probability of being associated with a malignancy, and thresholding said detections in said 3D image volume wherein only those detections whose probability is above said threshold are visualized.

According to a further aspect of the invention, the method comprises extracting 2D features from 2D image volume slices using machine learning algorithms, and providing these 2D features as inputs to said CAD algorithm.

According to a further aspect of the invention, the method comprises enhancing said X-ray breast images prior to constructing said 3D image volume.

According to a further aspect of the invention, the method comprises enhancing said 3D image volume prior to extracting 3D features from said image volume.

DETAILED DESCRIPTION OF EXEMPLARY EMBODIMENTS

Figure 1:
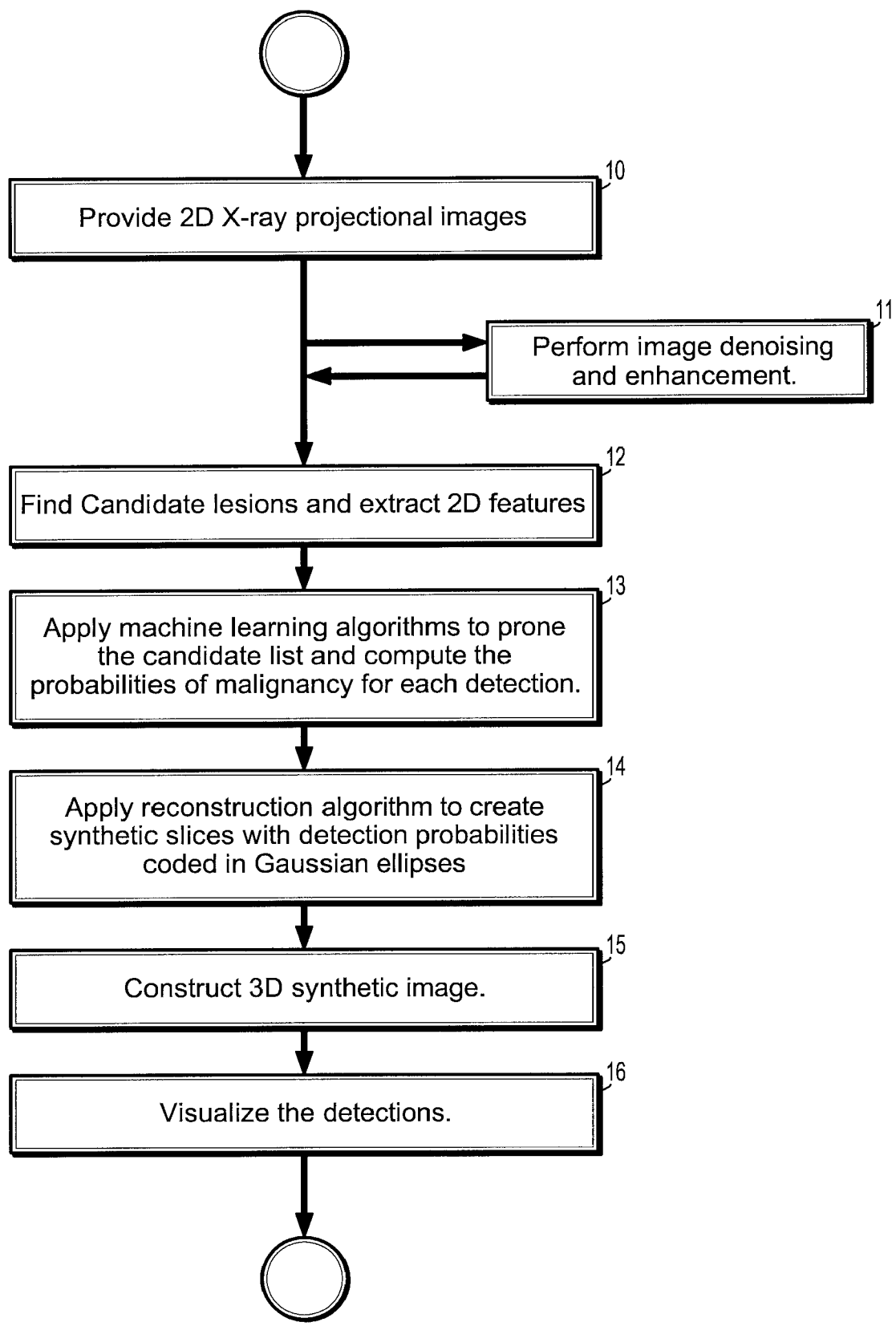
FIG. 1 is a flowchart illustrating an algorithm for detection of masses and calcifications in breast tomosynthesis images, according to an embodiment of the invention.

Exemplary embodiments of the invention as described herein generally include systems and methods for computer aided detection of masses and calcifications in tomosynthesis images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

According to an embodiment of the invention, original projection images can be analyzed by a 2-dimension (2D) computer-aided detection (CAD) algorithm to detect candidate malignancies. The detections, which comprise 2D locations and a malignancy probability, can be combined into a 3-dimensional (3D) representation using a reconstruction algorithm. A preprocessing step that may include histogram equalization, stretching and other image enhancement and noise reduction methods, can be applied before reconstruction as part of the CAD algorithm to enhance the image quality and reduce noise. As a result of the CAD algorithm, a probability of being a malignancy can be assigned to each detection in the 2D projection images. For each original projection image a 2D synthetic image is then created with a zero-density background and with ellipses containing the detected masses and calcifications. The density in the middle of the ellipse is equal to the detection probability, and gradually fades to zero toward the edges of ellipse. These constructed 2D synthetic images are then reconstructed into a 3D image using a reconstruction algorithm. In the resulting synthetic 3D image the voxels with the highest density will correspond to breast tissue most likely to contain a mass or calcification. The 3D synthetic image can be superimposed on the reconstructed 3D projection image of the breast and presented to a radiologist for viewing. Alternatively, a density threshold could be applied to the reconstructed synthetic image, and detections above the certain threshold could be highlighted on the reconstructed slices, maximum intensity projection views, oblique MPR, rendered 3D view of the breast, or any other 3D or 2D view which might help to visualize the detection for a radiologist.

According to another embodiment of the invention, the above method can be applied to reconstructed 2D images slices as well. In this case, one can omit the step involving the reconstruction of a 3D synthetic image from 2D synthetic images containing the detection probability coded in the form of ellipse densities. Instead, the 2D synthetic images are directly used as slices of synthetic 3D volume.

According to yet another embodiment of the invention, 3D CAD features such as 3D shape index, spicularity, eccentricity of super-scribed ellipse, texture features, normal intersection, gradient concentration, etc., can be computed for each detection. One possible group of features could be computed using a spherical transformation of a gray scale image and/or boundary/gradient image with a spherical coordinate transformation in 3D images or polar in 2D with coordinate system origin located at the center of the candidate detection. This spherical transformation allows a candidate tumor or lesion nodule to be in effect unrolled. The center could be determined from the peak probability amplitude of the Gaussian probability function inside the bounding ellipsoid. Band-pass or Gabor filters are then applied to detect location, amplitude and periodicity of the spiculations and locate the spikes of higher density coming from the center of the breast masses. Generally, mass spicularilty is linked to the probability of mass malignancy. Alternatively, a wavelet approach can help to detect length scales of the intensity/borderlgradient/curvature patterns in the spherical transformation in the neighborhood of each candidate location. These 3D features can be added to the 2D features or be used in conjunction with other 3D features to aid the computer aided detection of breast masses and calcifications.

FIG. 1 is a flowchart illustrating an algorithm for detection of masses and calcifications in breast tomosynthesis images, according to an embodiment of the invention. According to one embodiment of the invention, a sequence of 2D digital X-ray images acquired from different viewing angles is provided at step 10. The images are enhanced by various preprocessing techniques at step 11, such as the aforementioned steps of noise reduction, histogram equalization, stretching, etc. Note that this enhancement step is optional.

At step 12, simple features such as density, texture, etc. are extracted from an image and then clustering, region growing or connected component algorithms are applied to form candidate detections. Next, additional 2D features are extracted from the candidate lesions in 2D X-ray images. The 2D features include density, shape characteristics, texture, spicularity, of a candidate lesion as well as density and texture of the surrounding background, strength of boundaries (gradients), curvature, etc. These features are similar to the 3D features described above, but the key is that they are extracted from the original projection images, before possible information loss due to reconstruction. Then, at step 13, machine learning algorithms, such as classification algorithms previously trained on a training set containing known examples of the features for lesions identified by a physician, are then applied to the new candidate lesions to predict the probability of malignancy.

The steps above constitute an example of a computer-aided detection (CAD) algorithm for detecting possible tumors, lesions, calcifications, and other malignancies. Tumors and lesions are typically symmetric regions of increased density, while calcifications are characterized as clusters of bright dots. Tumors frequently include spikes radiating outward from the dense core. The results of steps 12 and 13 can be accomplished by known and commercially available CAD algorithms and products for CAD for detecting tumors in 2D mammography images. The CAD program typically outputs a series of locations in the 2D image that are potential malignancies, along with estimated probabilities of each location representing a malignancy. Alternatively, the CAD output is a probability map of each pixel in the 2D input image being part of a malignancy.

At step 14, a synthetic image is created from the CAD output where pixels with a malignancy probability below a threshold are assigned to be zero density, and with ellipses surrounding the above threshold regions containing the potential malignancy. The density within the ellipse is modeled with a 2D Gaussian whose peak corresponds to the pixels with highest probability of being malignant, with the amplitude of the Gaussian being equal to the malignancy probability. The Gaussian amplitude fades to the background amplitude toward the edge of the ellipse. These 2D synthetic images are constructed into a 3D image using an image reconstruction algorithm at step 15. Algorithms for image reconstruction are well known, and there are many products commercially available for accomplishing this task. In the resulting 3D image, the ellipses from 2D projections will merge in the places with higher likelihood of malignancy and form 3D amorphous shapes. The 3D synthetic image could be further analyzed to find the regions with highest density. These regions will likely correspond to breast tissue most likely to contain a malignant mass or calcification cluster.

At step 16, the 3D synthetic image can be superimposed on a 3D image reconstructed from the original set of 2D X-ray images as a visualization aid in viewing the image. Alternatively, a further density threshold can be applied to the synthetic image, and only those detections above the threshold would be highlighted.

Figure 2:
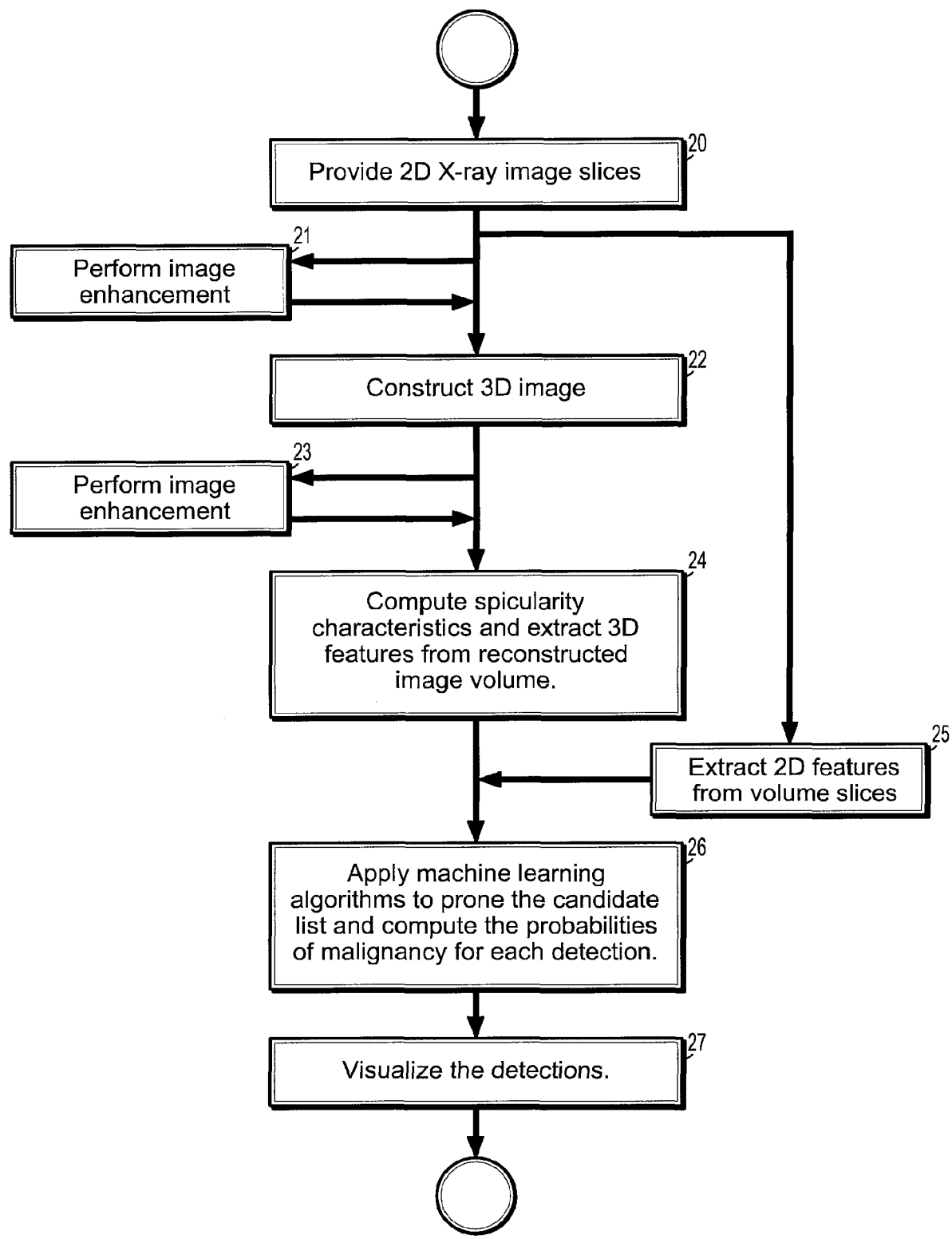
FIG. 2 is a flowchart illustrating other possible algorithms for detection of masses and calcifications in breast tomosynthesis images, according to an embodiment of the invention.

FIG. 2 is a flowchart illustrating other possible algorithms for detection of masses and calcifications in breast tomosynthetic images, according to an embodiment of the invention. According to an embodiment of the invention, a sequence of 2D digital X-ray images acquired from different viewing angles is provided at step 20. After an optional image enhancement of step 21, these 2D X-ray images are reconstructed into a 3D image at step 22 using an image reconstruction algorithm. The resulting 3D image can again be optionally enhanced at step 23. The resulting 3D image is represented as a series of consecutive 2D slices. At step 24, lesion candidates are extracted using clustering, region growing or connected component algorithms. Then 3D features are extracted from the candidate lesions. Next, at step 26, as in the 2D case, features are analyzed using machine learning algorithms, such as classification, previously trained on a training set to recognize the features of candidate lesions by comparison to known examples of the features of lesions marked by an expert radiologist. Examples of 3D features include shape characteristics, spicularity, eccentricity of super-scribed ellipse, texture features, normal intersection, gradient concentration, etc., as discussed above. The steps above constitute an example of a computer-aided detection (CAD) program for detecting possible tumors, lesions, calcifications, and other malignancies. As an optional step preceding the CAD step, 2D features can also be extracted at step 25 from slices of the reconstructed image volume and from the original projection images, and these 2D features can be included with the 3D features as input to a machine learning algorithm.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 3:
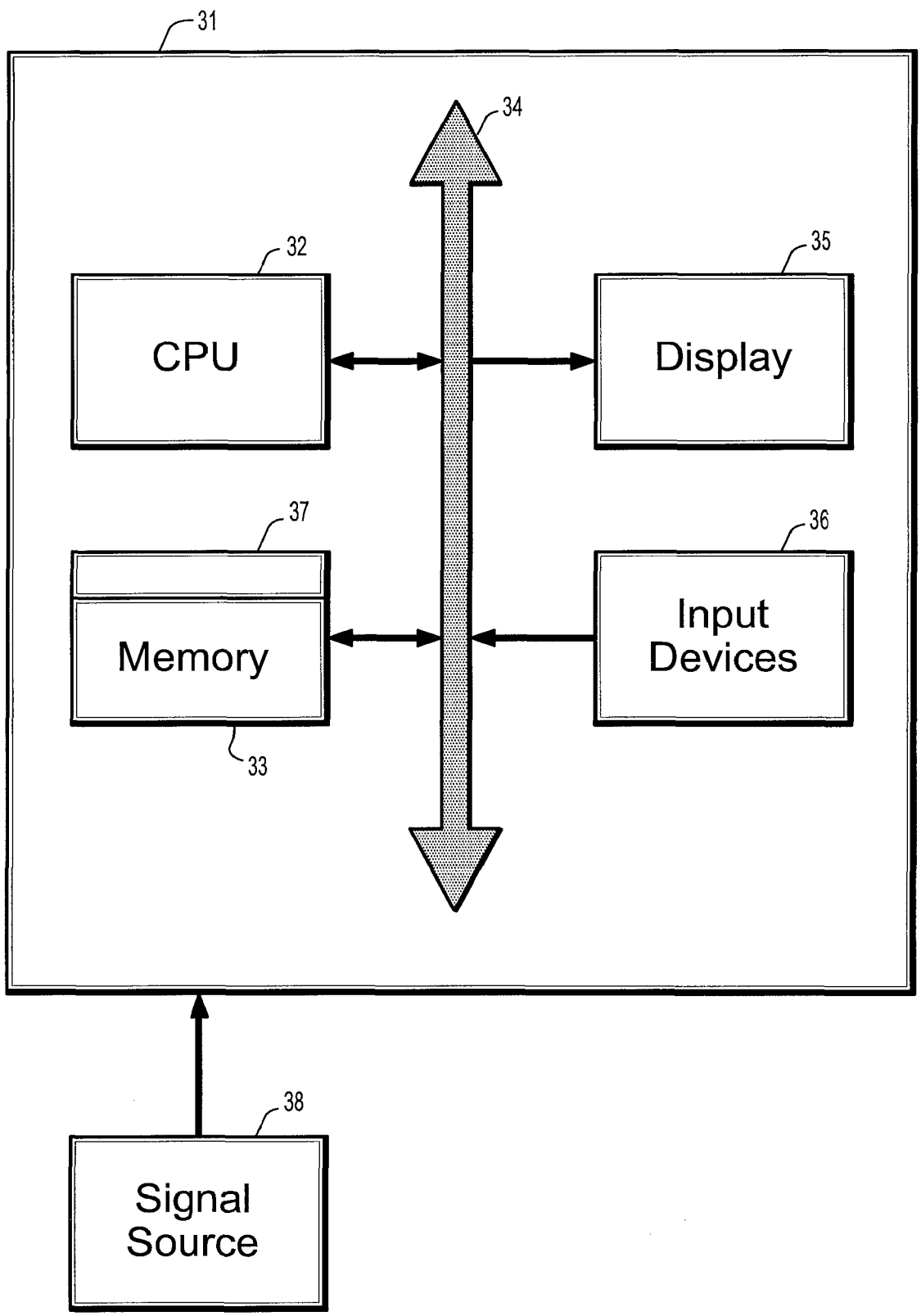
FIG. 3 is a block diagram of an exemplary computer system for implementing an algorithm for detection of masses and calcifications in tomosynthesis images, according to an embodiment of the invention.

FIG. 3 is a block diagram of an exemplary computer system for implementing an algorithm for detection of breast masses and calcifications in tomosynthesis images, according to an embodiment of the invention. Referring now to FIG. 3, a computer system 31 for implementing the present invention can comprise, inter alia, a central processing unit (CPU) 32, a memory 33 and an input/output (I/O) interface 34. The computer system 31 is generally coupled through the I/O interface 34 to a display 35 and various input devices 36 such as a mouse and a keyboard. The support circuits can include circuits such as cache, power supplies, clock circuits, and a communication bus. The memory 33 can include random access memory (RAM), read only memory (ROM), disk drive, tape drive, etc., or a combinations thereof. The present invention can be implemented as a routine 37 that is stored in memory 33 and executed by the CPU 32 to process the signal from the signal source 38. As such, the computer system 31 is a general purpose computer system that becomes a specific purpose computer system when executing the routine 37 of the present invention.

The computer system 31 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of detecting breast masses and calcifications in digitized images, comprising the steps of:
   providing a plurality of 2-dimensional (2D) digital X-ray projectional breast images acquired from different viewing angles, each said X-ray projectional image comprising a set of intensities on a 2D grid of pixels;
   extracting candidate lesions and 2D features from said 2D projectional images;
   computing spicularity characteristics of said candidate lesions, said characteristics including, but not limited to, location, periodicity, and amplitude;
   applying machine learning algorithms to said candidate lesions to predict a probability of malignancy of said lesion, wherein said learning algorithms have been trained on a training set containing known examples of the features for lesions identified by a physician;
   receiving from said learning algorithm a probability map of detections for each breast image, said detections comprising associating pixels with a probability of being associated with a malignancy;
   creating a synthetic 2D slice for each X-ray image wherein malignant regions are indicated by ellipses on a non-malignant background; and
   constructing a synthetic 3-dimensional (3D) image volume from said 2D synthetic slices.

2. The method of claim 1, wherein said probability map associates each pixel on each 2D X-ray image with a probability of being associated with a malignancy.

3. The method of claim 1, wherein said probability map returns a list of pixel locations and associated malignancy probabilities, wherein only those locations with malignancy probabilities above a threshold are returned.

4. The method of claim 1, further comprising constructing a 3D image from said 2D X-ray breast images, and superimposing said 3D synthetic image on said constructed 3D X-ray image.

5. The method of claim 1, further comprising thresholding said detections in said 3D synthetic image wherein only those detections whose probability is above said threshold are visualized.

6. The method of claim 1, wherein the malignancy probability in said malignant regions are represented by Gaussian functions inside said ellipses, wherein a peak amplitude of each said Gaussian corresponds to the pixel within said ellipse with a maximum probability of being associated with said malignancy, and whose probability amplitude decreases smoothly to a background value.

7. The method of claim 6, wherein constructing said synthetic 3D image comprises seeking those 2D ellipses in those 2D synthetic slices that overlap in said 3D synthetic image, representing those 3D regions formed by overlapping 2D ellipses by 3D ellipsoids, representing the malignancy probability within each 3D ellipsoid by a 3D Gaussian whose probability amplitude decreases smoothly from a peak value within said ellipsoid to a background value.

8. The method of claim 1, wherein said spicularity characteristics are computed using a spherical or polar coordinate transformation on said lesion followed by band pass filtering on the intensity or gradient of said transformed lesion.

9. The method of claim 1, further comprising enhancing said X-ray breast images prior to extracting said 2D features.

10. A method of detecting breast masses and calcifications in digitized images, comprising the steps of:

providing a plurality of 2-dimensional (2D) digital X-ray breast images acquired from different viewing angles, said X-ray image comprising a set of intensities on a 2D grid of pixels;

constructing a 3-dimensional (3D) image volume from said 2D X-ray breast images;

computing spicularity characteristics of said candidate lesions, said characteristics including, but not limited to, location, periodicity, and amplitude;

extracting 3D features from said image volume using a machine learning algorithm;

applying machine learning algorithms to said candidate lesions to predict a probability of malignancy of said lesion, wherein said learning algorithms have been trained on a training set containing known examples of the features for lesions identified by a physician;

receiving from said learning algorithm a probability map of detections for each breast image, said detections comprising associating pixels with a probability of being associated with a malignancy; and thresholding said detections in said 3D image volume wherein only those detections whose probability is above said threshold are visualized.

11. The method of claim 10, further comprising extracting 2D features from 2D image volume slices using machine learning algorithms, and providing these 2D features as inputs to said CAD algorithm.

12. The method of claim 10, further comprising enhancing said X-ray breast images prior to constructing said 3D image volume.

13. The method of claim 10, further comprising enhancing said 3D image volume prior to extracting 3D features from said image volume.

14. A program storage device readable by a computer, tangibly embodying a program of instructions executable by the computer to perform the method steps for detecting breast masses and calcifications in digitized images, said method comprising the steps of:

providing a plurality of 2-dimensional (2D) digital X-ray projectional breast images acquired from different viewing angles, each said X-ray projectional image comprising a set of intensities on a 2D grid of pixels;

extracting candidate lesions and 2D features from said 2D projectional images;

computing spicularity characteristics of said candidate lesions, said characteristics including, but not limited to, location, periodicity, and amplitude;

applying machine learning algorithms to said candidate lesions to predict a probability of malignancy of said lesion, wherein said learning algorithms have been trained on a training set containing known examples of the features for lesions identified by a physician;

receiving from said learning algorithm a probability map of detections for each breast image, said detections comprising associating pixels with a probability of being associated with a malignancy;

creating a synthetic 2D slice for each X-ray image wherein malignant regions are indicated by ellipses on a non-malignant background; and constructing a synthetic 3-dimensional (3D) image volume from said 2D synthetic slices.

15. The computer readable program storage device of claim 14, wherein said probability map associates each pixel on each 2D X-ray image with a probability of being associated with a malignancy.

16. The computer readable program storage device of claim 14, wherein the probability map returns a list of pixel locations and associated malignancy probabilities, wherein only those locations with malignancy probabilities above a threshold are returned.

17. The computer readable program storage device of claim 14, the method further comprising constructing a 3D image from said 2D X-ray breast images, and superimposing said 3D synthetic image on said constructed 3D X-ray image.

18. The computer readable program storage device of claim 14, the method further comprising thresholding said detections in said 3D synthetic image wherein only those detections whose probability is above said threshold are visualized.

19. The computer readable program storage device of claim 14, wherein the malignancy probability in said malignant regions are represented by Gaussian functions inside said ellipses, wherein a peak amplitude of each said Gaussian corresponds to the pixel within said ellipse with a maximum probability of being associated with said malignancy, and whose probability amplitude decreases smoothly to a background value.

20. The computer readable program storage device of claim 19, wherein constructing said synthetic 3D image comprises seeking those 2D ellipses in those 2D synthetic slices that overlap in said 3D synthetic image, representing those 3D regions formed by overlapping 2D ellipses by 3D ellipsoids, representing the malignancy probability within each 3D ellipsoid by a 3D Gaussian whose probability amplitude decreases smoothly from a peak value within said ellipsoid to a background value.

21. The computer readable program storage device of claim 14, wherein said spicularity characteristics are computed using a spherical or polar coordinate transformation on said lesion followed by band pass filtering on the intensity or gradient of said transformed lesion.

22. The computer readable program storage device of claim 14, the method further comprising enhancing said X-ray breast images prior to extracting said 2D features.

\* \* \* \* \*